(12) United States Patent
Kari

(10) Patent No.: US 7,270,477 B1
(45) Date of Patent: *Sep. 18, 2007

(54) X-RAY DETECTOR METHODS AND APPARATUS

(75) Inventor: Nirmal Mukund Kari, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/445,359

(22) Filed: Jun. 1, 2006

(51) Int. Cl.
*G03B 42/04* (2006.01)

(52) U.S. Cl. ...................... 378/167; 378/204
(58) Field of Classification Search ............ 378/98.8, 378/167, 189, 204; 250/370.09
See application file for complete search history.

(56) References Cited

U.S. PATENT DOCUMENTS

| 2005/0117709 | A1 | 6/2005 | Dippl et al. ............... 378/189 |
| 2005/0135564 | A1 | 6/2005 | Dippl et al. ............... 378/167 |
| 2006/0065846 | A1 | 3/2006 | Ertel et al. ............ 250/370.11 |
| 2006/0070384 | A1 | 4/2006 | Ertel ........................... 62/3.3 |
| 2006/0071172 | A1 | 4/2006 | Ertel et al. ............ 250/370.11 |
| 2006/0104416 | A1 | 5/2006 | Kump et al. ................. 378/91 |
| 2006/0109958 | A1 | 5/2006 | Ertel et al. ................. 378/205 |

*Primary Examiner*—Courtney Thomas
(74) *Attorney, Agent, or Firm*—Fisher Patent Group, LLC; Thomas M. Fisher

(57) ABSTRACT

Apparatus includes a digital x-ray detector holder configured to hold x-ray detectors of at least two different sizes, wherein the holder is user positionable and is user lockable to maintain a user positioned relationship between the holder and an x-ray source.

20 Claims, 4 Drawing Sheets

US 7,270,477 B1

X-RAY DETECTOR METHODS AND APPARATUS

BACKGROUND OF THE INVENTION

This invention relates generally to methods and apparatus for digital x-ray imaging systems, and more particularly to methods and apparatus for positioning and holding stationary (while performing an imaging operation) a digital x-ray detector.

X-ray devices have moved from being fixed devices to being portable devices. The portable X-ray detector allows a host of new and exciting applications wherein the detector can be positioned not only under the patient but also perpendicular to the patient. This will allow the radiologist to acquire lateral, sagittal and oblique views of the anatomy. In other words, it is not the patient that moves in-order to acquire his/her x-ray images but instead it is the detector that is held up and "positioned" appropriately. Any one who has had a fracture and has been asked to rotate the broken limb to acquire a perpendicular view will immediately understand how painful the request is. In the case of serious injuries, and in emergency rooms and ICU's the need for patient immobility is not just a convenience but an important aspect. It is highly desirable for patients with broken limbs and for post-surgical patients to be kept immobile.

There are two problems that arise when positioning the portable detector: 1. Manually holding up a detector causes motion artifacts in the acquired image; and 2. The detector is heavy to hold, and the radiologist cannot hold a 15-pound detector and shoot x-rays very effectively at the same time.

Therefore described below are methods and apparatus for positioning and holding a digital x-ray detector.

BRIEF DESCRIPTION OF THE INVENTION

In one aspect, apparatus includes a digital x-ray detector holder configured to hold x-ray detectors of at least two different sizes, wherein the holder is user positionable and is user lockable to maintain a user positioned relationship between the holder and an x-ray source.

In another aspect, a digital x-ray imaging system is provided. The system includes an x-ray source, a digital x-ray detector holder configured to hold x-ray detectors of at least two different sizes, wherein the holder is user positionable and is user lockable to maintain a user positioned relationship between the holder and the x-ray source, and a digital x-ray detector is positioned in the holder.

In still another aspect, a kit includes a digital detector holder, a tripod configured to attach to the holder, a wall mount configured to attach to the holder, and a bed mount configured to attach to the holder.

DETAILED DESCRIPTION OF THE INVENTION

There are herein provided methods and apparatus useful for a digital x-ray system. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Figure 1:
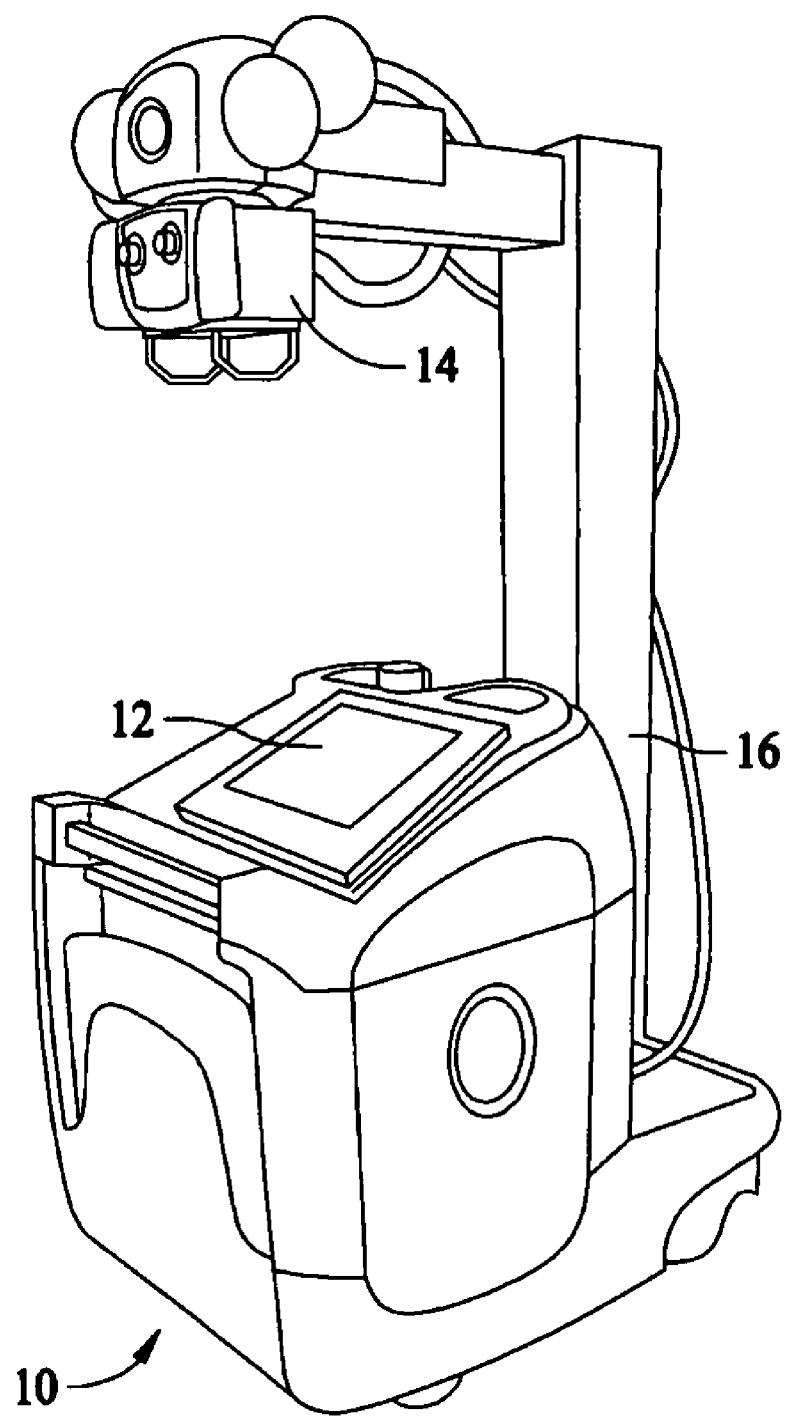
FIG. 1 illustrates a known portable digital x-ray imaging system.

FIG. 1 illustrates a known portable digital x-ray imaging system 10 including an operator console 12, an x-ray source 14, and x-ray source positioning arm. In one embodiment, system 10 is a Definium™ AMX 800 system commercially available from the General Electric Company.

Figure 2:
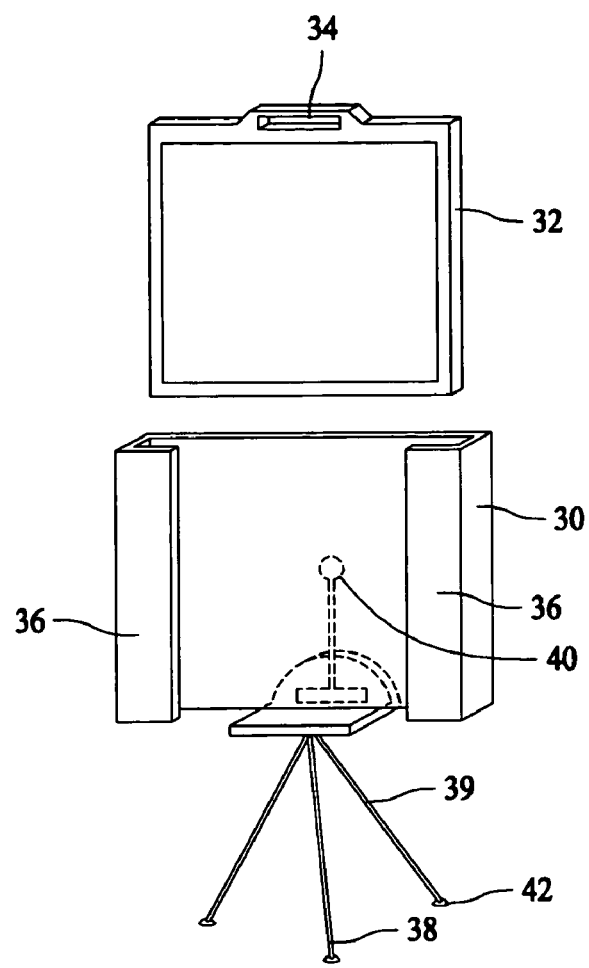
FIG. 2 illustrates a detector holder (also referred herein as a positioner).

FIG. 2 illustrates a detector holder 30 (also referred herein as a positioner because holder 30 both is used to hold and position a detector 32). Detector 32 may include a handle 34. In addition, one embodiment has a handle on holder 30. A plurality of sidewalls 36 extend from the sides of holder 30 and leave a opening from which x-rays can pass and impinge detector 32. Holder 30 can fit detectors of different sizes, and while shown in FIG. 2 as only holding different height detectors, in another embodiment, holder 30 is at least a two piece apparatus and can be slidably (or otherwise) adjusted to fit different width detectors. Holder 30 is mounted to a tripod 38 via a ball and socket mechanism 40 (better seen in other Figures). Of course, other mounting mechanisms may be used as long as the mounting mechanism is flexible so that the held detector is positionable. As better explained below, an electric cord 39 may be attached to holder 30. Feet 42 are at the ends of the legs of tripod 38. In one embodiment, feet 42 have a non skid material to improve stability of tripod 38. In another embodiment, feet 42 include lockable wheels like those found on a baby stroller or a ping-pong table. The lockable wheels allow for both an easy positioning of tripod 38 when unlocked and for stability when locked.

Figure 3:
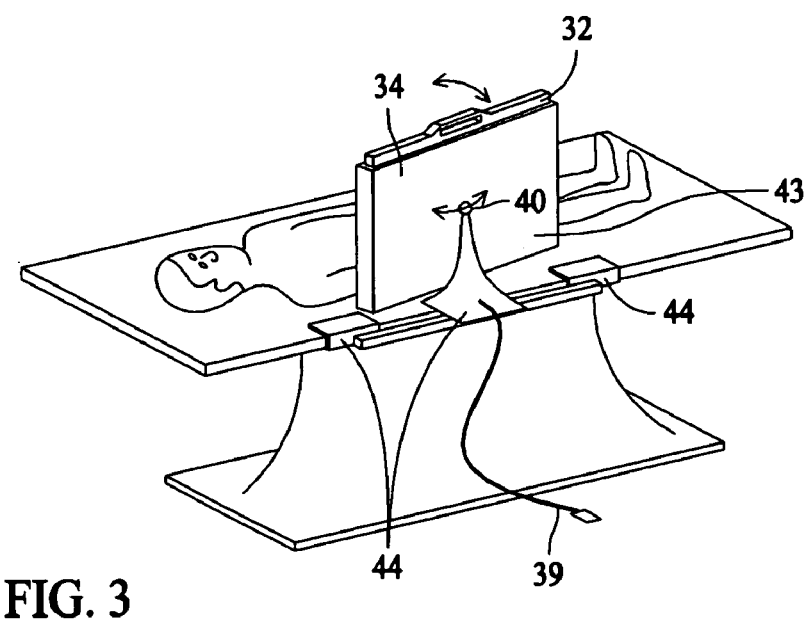
FIG. 3 illustrates the holder mounted to a bed mount.

FIG. 3 illustrates holder 30 mounted to a bed mount 43 that may include at least one bed clamp 44. Arrows in FIG. 3 illustrates the positioner 30 is free to move in all three dimensions and has three degrees of freedom.

Figure 4:
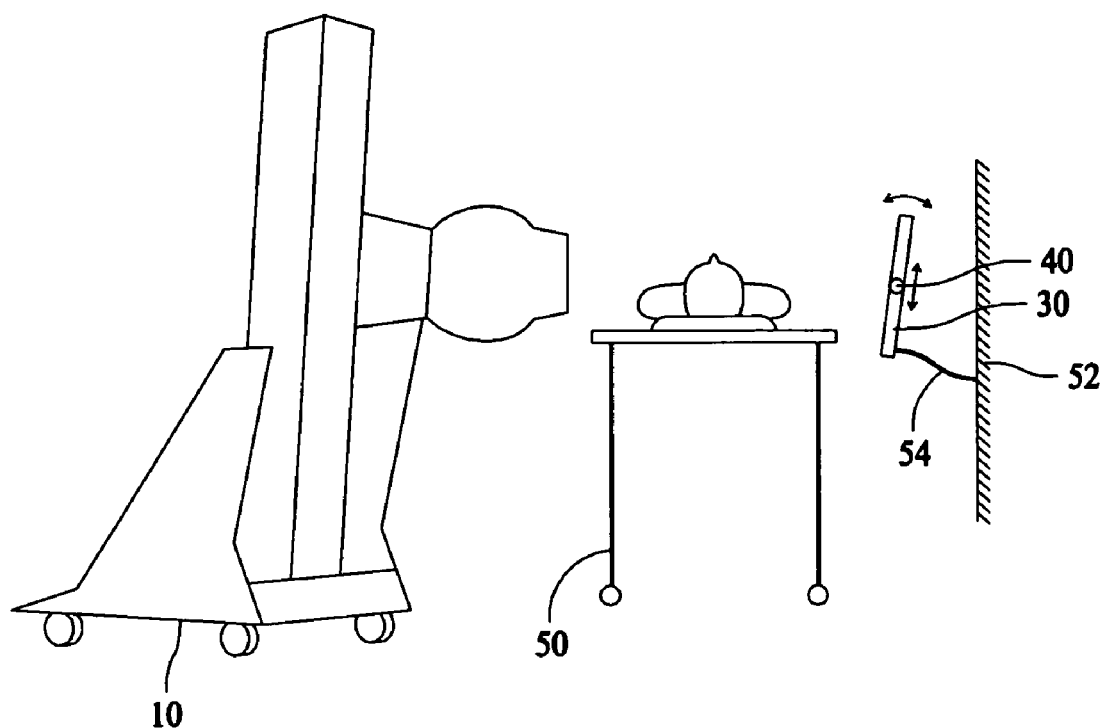
FIG. 4 illustrates a system used to image a patient (or other object).

FIG. 4 illustrates system 10 used to image a patient (or other object) on a table 50 by emitting x-rays that impinge the detector held in holder 30 when mounted to a wall 52 via a wall mount 54. Note holder 30 is configured to hold x-ray detectors of at least two different sizes, wherein the holder is user positionable and is user lockable to maintain a user positioned relationship between the holder and an x-ray source. Holder 10 is configured to do that in all the Figures not just FIG. 4.

Figure 5:
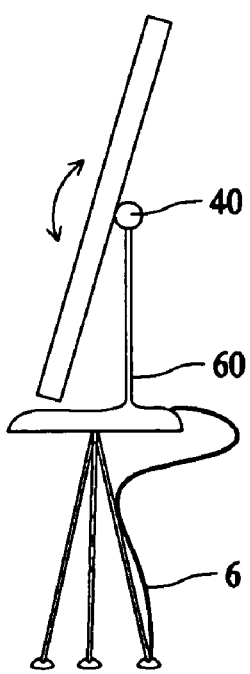
FIG. 5 illustrates an optional battery charger coupled to the holder.

FIG. 5 illustrates an optional battery charger 60 coupled to holder 30. In one embodiment, instead of a charger 60, holder may include a battery. In either embodiment, the battery is used to power the detector. However the charger embodiment includes the electric plug 39 as mentioned above in reference to FIG. 2. Holder 30 may include electrical contacts that the battery connects with automatically as the detector is positioned in holder 30, or may include a wire connector (a plug) to make the connection.

Figure 6:
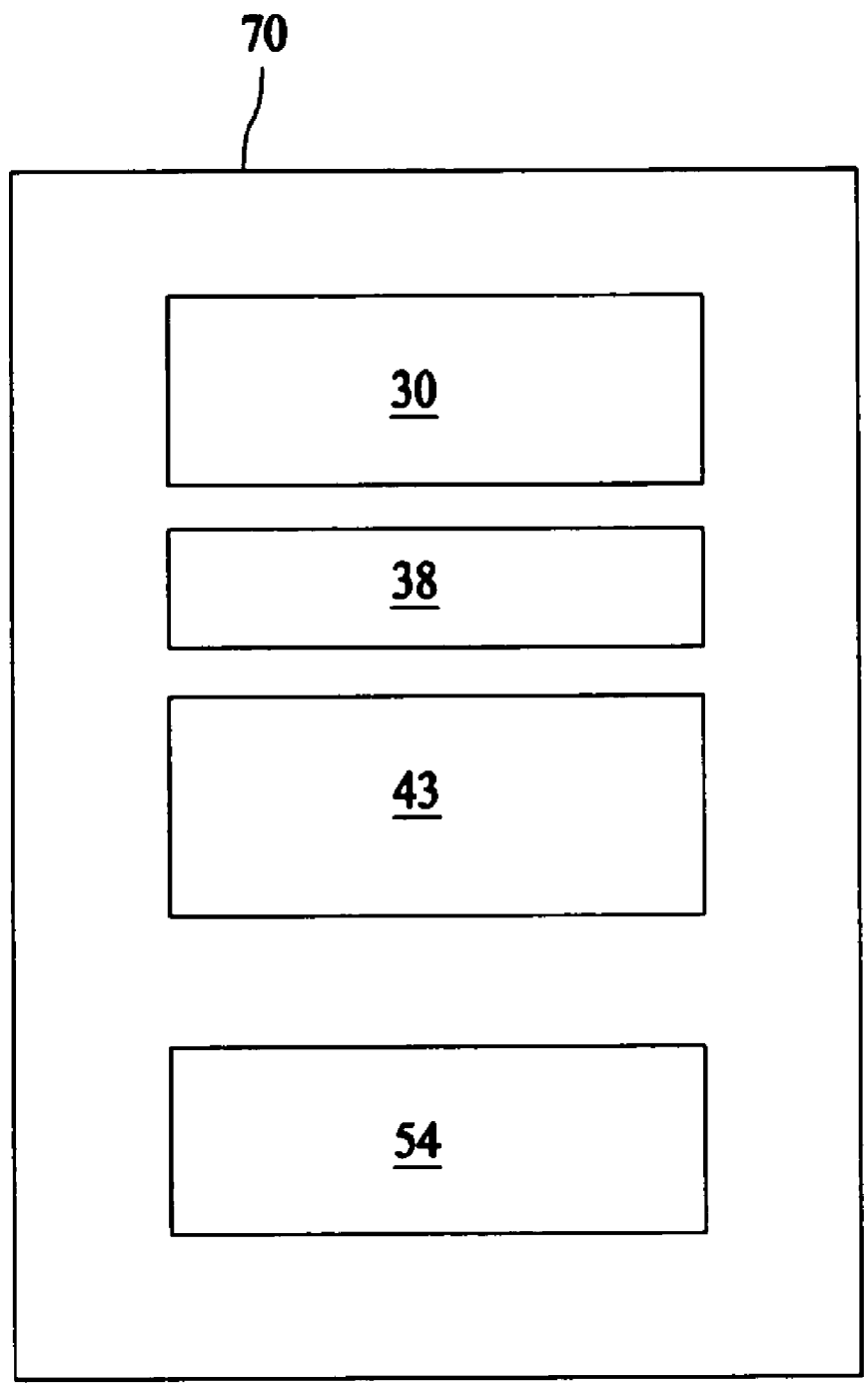
FIG. 6 illustrates a kit.

It is contemplated that purchasers may wish to purchase holder 30 with tripod 38, bed mount 43, and wall mount 54 as a kit. Therefore, such a kit 70 is illustrated in FIG. 6. Of course, in such an embodiment, tripod 38 and mounts 43 and 54 are all interchangeable and mount to holder 40 in a ball and socket mechanism 40. However, it is contemplated that the benefits of the invention accrue to other embodiments, and in one embodiment, tripod and/or mounts 43 and 54 may be configured to use different methods of attaching to holder 30. Both different from a ball and socket mechanism, and different from each other in respect to manner and location on holder 30.

The disclosure proposes a positioner for the portable x-ray detector that will allow a single radiologist to slide the detector in a holder that is mounted on a stand or clamped on a bed. The positioner will allow the radiologist to adjust the position and orientation of the detector to suit the application, just as a photographer uses a tri-pod stand to position the camera before he takes the shot. The positioner will have a locking mechanism to fix the final position of the detector vis a vis the x-ray generator so that there are no motion artifacts caused by the relative motion between the source and detector. The positioner frees the radiologist to take the exposure and be well away from the path of the X-rays.

In accordance with different embodiments, the basic parts of the positioner may include:

1) A holder casing in to which detectors of various sizes can slide into. The casing will be adjustable to allows detectors of varying widths to fit snuggly. The holder is rotated in 3-dimensional degrees of freedom via a ball and socket mechanism for oblique angles.

2) Tripod stand to position the holder at the appropriate height.

3) Bed clamps in case the holder is to be positioned at the patient bed.

4) Locking mechanism that will fix the position of the detector vis a vis the X-ray generator at the time of exposure.

5) Optional battery charger in case the detector is battery operated and needs to be charged while exposing. And 6) Wall-side positioner mechanism that may be used without the tripod.

Technical effects include:

1) Removes radiologist from the path of the x-ray.

2) Removes the need for patient to move with respect to the detector.

3) Reduces any motion artifact caused when due to relative movement between the source and the detector.

4) Allows the radiologist to adjust the position of the x-ray and take the shot without any assistance.

5) No need for the radiologist to hold up the heavy detector during exposure.

6) Less chance of drop and detector damage when the detector is on the positioner case and stand.

It is contemplated that the benefits of the invention accrue to both medical imaging systems and non-medical imaging systems such as those systems typically employed in an industrial setting or a transportation setting, such as, for example, but not limited to, a baggage scanning digital x-ray imaging system for an airport or other transportation center. Additionally, although described in the content of Human patients, it is contemplated that the benefits of the invention accrue to small animal scanners.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. Apparatus comprising:
a digital x-ray detector holder configured to hold x-ray detectors of at least two different sizes, wherein said holder is user positionable and is user lockable to maintain a user positioned relationship between said holder and an x-ray source.

2. Apparatus in accordance with claim 1 wherein said holder is positionable in 3-dimension degrees of freedom via a ball and socket mechanism.

3. Apparatus in accordance with claim 2 further comprising a tripod stand connected to said holder.

4. Apparatus in accordance with claim 1 further comprising a wall mount connected to said holder and to a wall.

5. Apparatus in accordance with claim 1 further comprising a clamp connectable to a bed.

6. Apparatus in accordance with claim 5 further comprising a battery coupled to said holder.

7. Apparatus in accordance with claim 1 further comprising a battery charger coupled to said holder, said battery charger configured to provide power to a detector battery.

8. A digital x-ray imaging system comprising:
an x-ray source;
a digital x-ray detector holder configured to hold x-ray detectors of at least two different sizes, wherein said holder is user positionable and is user lockable to maintain a user positioned relationship between said holder and the x-ray source; and
a digital x-ray detector positioned in said holder.

9. A system in accordance with claim 8 wherein said holder is positionable in 3-dimension degrees of freedom via a ball and socket mechanism.

10. A system in accordance with claim 9 further comprising a tripod stand connected to said holder.

11. Apparatus in accordance with claim 8 further comprising a wall mount connected to said holder and to a wall.

12. A system in accordance with claim 8 further comprising a clamp connectable to a bed.

13. Apparatus in accordance with claim 12 further comprising a battery charger coupled to said holder.

14. Apparatus in accordance with claim 8 further comprising a battery charger coupled to said holder, said battery charger configured to charge a detector battery.

15. A kit comprising:
a digital detector holder;
a tripod configured to attach to said holder;
a wall mount configured to attach to said holder; and
a bed mount configured to attach to said holder.

16. A kit in accordance with claim 15 wherein said tripod, said wall mount, and said bed mount all attach to the same place on said holder.

17. A kit in accordance with claim 15 further comprising at least one of a battery and a battery charger.

18. A kit in accordance with claim 15 wherein said tripod, said wall mount, and said bed mount all attach to the same place on said holder via a ball and socket mechanism.

19. A kit in accordance with claim 15 wherein said holder is user positionable and is user lockable to maintain a user positioned relationship between said holder and an x-ray source.

20. A kit in accordance with claim 19 wherein said tripod, said wall mount, and said bed mount all attach to the same place on said holder via a ball and socket mechanism.

* * * * *